US009333283B2

(12) United States Patent
Cook et al.

(10) Patent No.: US 9,333,283 B2
(45) Date of Patent: May 10, 2016

(54) BREAST PUMP

(75) Inventors: Graham Cook, Harlow (GB); Ian Philip Darnell, Cambridge (GB); Mark Robert Gabriel Douglas, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 106 days.

(21) Appl. No.: 13/878,856

(22) PCT Filed: Oct. 10, 2011

(86) PCT No.: PCT/IB2011/054443
§ 371 (c)(1),
(2), (4) Date: Jun. 4, 2013

(87) PCT Pub. No.: WO2012/049606
PCT Pub. Date: Apr. 19, 2012

(65) Prior Publication Data
US 2013/0245548 A1  Sep. 19, 2013

(30) Foreign Application Priority Data
Oct. 15, 2010  (EP) ..................................... 10187716

(51) Int. Cl.
*A61M 1/06* (2006.01)
*A61M 1/00* (2006.01)
(52) U.S. Cl.
CPC ............... *A61M 1/06* (2013.01); *A61M 1/0072* (2014.02); *A61M 1/066* (2014.02)

(58) Field of Classification Search
CPC ...... A61M 1/0072; A61M 1/06; A61M 1/066
USPC ........................................................ 604/74–76
See application file for complete search history.

(56) References Cited

U.S. PATENT DOCUMENTS

| 4,813,932 A  * | 3/1989 | Hobbs ............................. 604/74 |
| 7,029,454 B2 | 4/2006 | Watanabe |
| 2005/0154349 A1 | 7/2005 | Renz et al. |
| 2006/0116632 A1 | 6/2006 | Gillian |
| 2007/0060873 A1 | 3/2007 | Hiraoka et al. |
| 2008/0243059 A1 | 10/2008 | Yamashita et al. |

FOREIGN PATENT DOCUMENTS

| EP | 1661590 A1 | 5/2006 |
| GB | 2166353 A | 5/1986 |
| JP | 484639 | 2/1973 |
| JP | H039764 A | 1/1991 |
| JP | 2002336347 A | 11/2002 |
| WO | 8808312 A1 | 11/1988 |
| WO | 2008057218 A2 | 5/2008 |
| WO | 2010054174 A1 | 5/2010 |

* cited by examiner

*Primary Examiner* — Rebecca E Eisenberg

(57) ABSTRACT

The present invention relates to a breast pump. The breast pump comprises a main body (21), a breast receiving funnel (23) extending from the main body (21), and a nipple receiving chamber (34) formed in the main body (21) to receive a user's nipple. The funnel (23) and the main body (21) are configured so that at least a portion of a user's nipple is received in the nipple receiving chamber (34) when a user's breast is disposed in the breast receiving funnel (23).

12 Claims, 6 Drawing Sheets

ID OF THE INVENTION

The present invention relates to a breast pump. In particular, the present invention relates to a breast pump which is operable to extract milk from a breast of a user.

BACKGROUND OF THE INVENTION

Breast pumps are well known devices for extracting milk from a breast of a user. A breast pump may be used if the baby or infant is not itself able to express milk from the breast, or if the mother is separated from the baby or infant, for example, if away from the baby at work. The use of a breast pump to express milk may also be used to stimulate and increase milk production in women with a low milk supply.

Breast pumps make use of a vacuum to induce milk expression from a nursing mother's breast. The pumping action of the device draws the milk from the nipple to a collection vessel, and the pressure and/or frequency may generally be adjusted to the preferences of the mother.

A known breast pump for extracting milk from a user's breast is shown in FIG. 1. Such a breast pump 1 comprises a main body 2 and a collection vessel 3, such as a feeding bottle or bag. The collection vessel 3 is attached to the main body 2 by a screw fitting.

A breast-receiving funnel 4 extends from the main body 2 for receiving the breast of a user. The funnel 4 has an inner surface 5 and comprises a mouth 6 and a neck 7. The mouth 6 is open at an outer end and the inner surface 5 of the funnel 4 converges from the outer end towards the neck 7 to form a hollow recess in which a breast is received.

The neck 7 is a generally cylindrical tube which extends from the mouth 6 to the main body 2. When a breast of a user (not shown) is received in the mouth 6 of the funnel, the nipple of a user is received in a nipple receiving space 8 defined by the neck 7 of the funnel 4.

A fluid path is defined by the mouth 6 and neck 7 of the funnel 4, through the main body 2, to the collection vessel 3 so that milk induced from a user's breast flows along the neck of the funnel 4, through the main body 2 to the collection vessel 3.

A vacuum pump unit 9 is formed in the main body 2 and generally comprises a resilient diaphragm 10 which is deformable in a vacuum chamber formed in the main body 2 along the fluid path to create a vacuum in the vacuum chamber, and therefore along the fluid path, by means of a user manually operating a handle 11 which acts on the diaphragm 10, or by means of an electric motor (not shown). A one way valve 12 is disposed along the fluid path between the vacuum chamber and the collection vessel 3 to prevent a vacuum being created in the collection vessel 3, but to allow milk to flow along the fluid path into the collection vessel 3.

However, a problem with known breast pump arrangements is that they need to be used with the user sat in an upright position or with the user leaning forwards, as shown in FIG. 1, to maximize the volume of expressed milk that flows through to the collection vessel 3. Generally, if a user does not lean forward then the milk flows back towards the breast due to the inner surface 5 of the neck 7 of the funnel 4 forming an opposing incline, as shown in FIG. 2. This leads to milk pooling at the breast, leakage from the mouth 6 of the funnel 4 around the user's breast and ultimately loss of milk.

Expressed milk is considered to be very precious and is known to have a high emotional value to mothers that have expressed milk from their breasts. Therefore, this residual milk is considered to be a loss to a user, and this loss of milk may have an emotional impact on the user.

Furthermore, leaning forward for the full expression duration of 15 to 30 minutes is uncomfortable and prevents a user from relaxing. In order for milk to be produced in the milk glands to be released into the milk ducts a let-down' reflex has to occur. However, it is known that the time to 'let down reflex' will increase and milk production will be inefficient if the mother is uncomfortable and not relaxed.

A breast pump system is known from US 2006/0116632 A1 which attempts to deal with the above problems, and allow a user to recline whilst using a breast pump by use of an insert for the breast pump and a strap arrangement. However, a problem with the breast pump system in this document is that a breast pump in which the insert is disposed must be maintained in an upright position to prevent pooling, even when a user is in a reclined position. Therefore, the angle at which the user is able to lean back is limited before the breast pump abuts against the user's midriff.

A further disadvantage of the breast pump system recited in the above document is that the user's nipple extending into the insert of the breast pump system will contact and abut against the insert, which may cause abrasion or rubbing of the user's nipple and cause discomfort and/or soreness. Furthermore, two breast pumps must be used simultaneously in order for the breast pump system to operate successfully.

SUMMARY OF THE INVENTION

Therefore, it is an object of the invention to provide a breast pump which substantially alleviates or overcomes the problems mentioned above.

According to the present invention, there is provided a breast pump comprising a main body, a breast receiving funnel extending from the main body, a nipple receiving chamber formed in the main body to receive a user's nipple, and a fluid passageway extending from the nipple receiving chamber for receiving milk expressed from a user's nipple, wherein the funnel and the main body are configured so that at least a portion of a user's nipple is received in the nipple receiving chamber when a user's breast is disposed in the breast receiving funnel and the fluid passageway extends substantially along the nipple receiving chamber so that at least a portion of a user's nipple extends over the fluid passageway when a user's nipple is disposed in the nipple receiving chamber.

Preferably, the nipple receiving chamber has an opening to the funnel through which a user's nipple is receivable, an end wall and a wall extending from the opening to the end wall, the fluid passageway extending substantially along the wall between the opening and the end wall.

Conveniently, an edge of the fluid passageway is formed adjacent to the opening with the funnel.

Advantageously, the breast receiving funnel comprises a mouth and a neck, the neck extending between the mouth and the nipple receiving chamber, and the funnel being configured so that a user's nipple extends through the neck into the nipple receiving chamber when a user's breast is disposed in the funnel.

Preferably, the main body further comprises a connection means for connecting a milk collection vessel, wherein the fluid passageway communicating between the nipple receiving chamber and a milk collection vessel when a milk connection vessel is attached to the main body.

The breast pump may further comprise a one-way valve disposed in the fluid passageway.

The breast pump may further comprise a vacuum pump unit to generate a vacuum in the nipple receiving chamber.

In one embodiment, the vacuum pump unit comprises a deformable diaphragm, the deformable diaphragm being disposed in a diaphragm chamber spaced from the nipple receiving chamber.

A vacuum pathway may communicate the vacuum pump unit with the nipple receiving chamber.

Advantageously, the nipple receiving chamber is disposed between the fluid passageway and the vacuum pathway.

Conveniently, the vacuum pathway extends from the side wall of the nipple receiving chamber.

Preferably, the vacuum pathway extends from an opposing side of the nipple receiving chamber to the fluid passageway.

BRIEF DESCRIPTION OF THE DRAWINGS

Preferred embodiments of the invention will now be described, by way of example only, with reference to the accompanying drawings, in which.

DETAILED DESCRIPTION OF THE EMBODIMENTS

Figure 1:
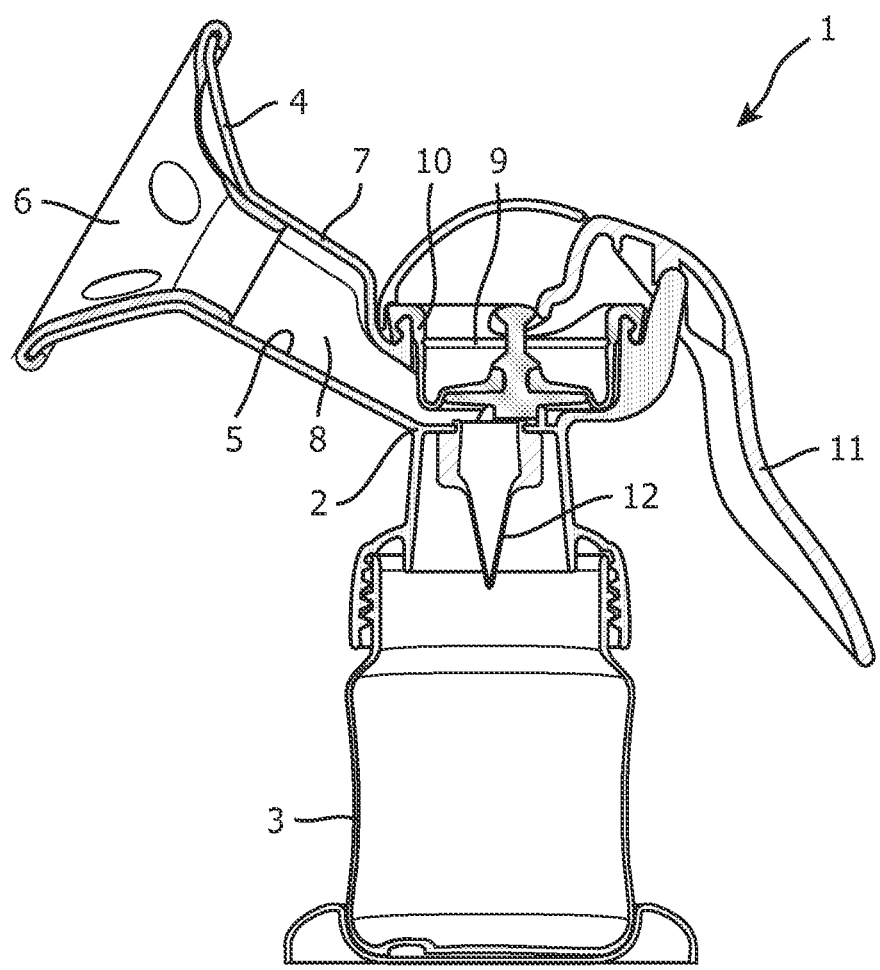
FIG. 1 shows a cross-sectional side view of an existing breast pump.
Figure 2:
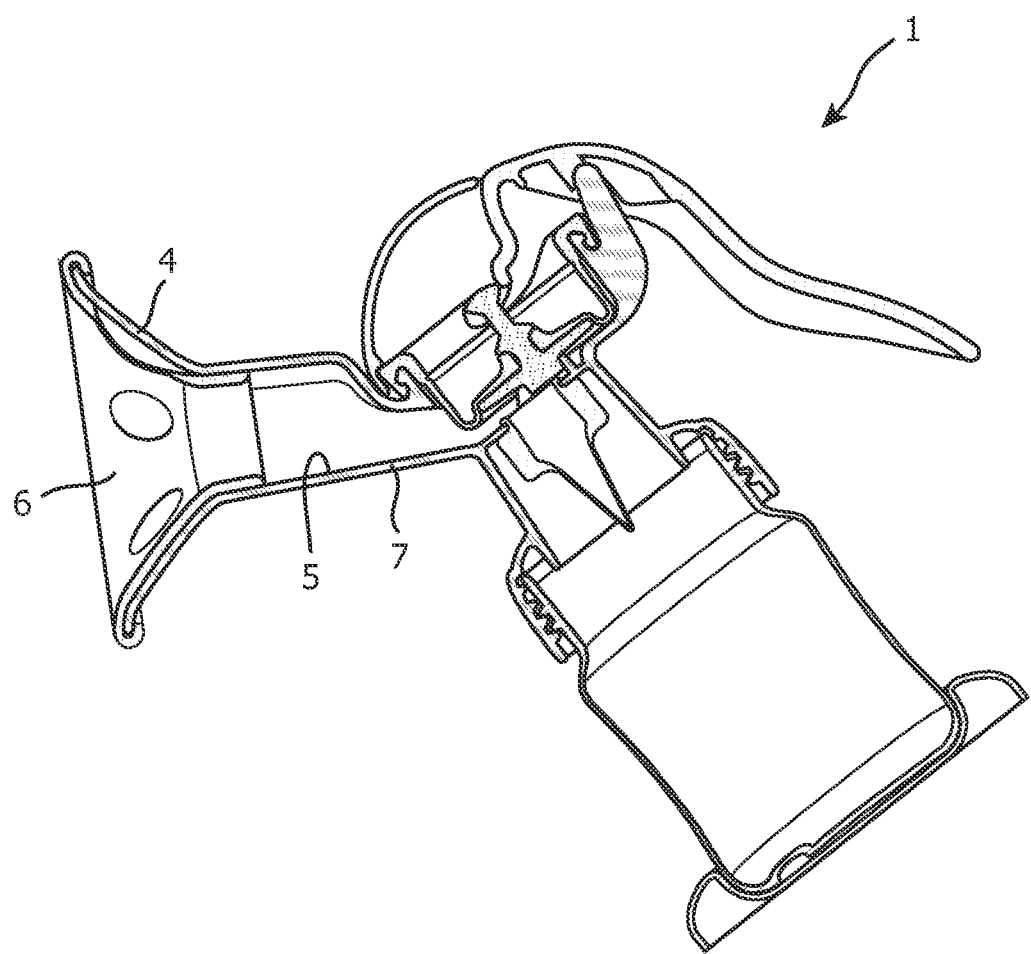
FIG. 2 shows a cross-sectional side view of the existing breast pump shown in FIG. 1 inclined at an angle.
Figure 3:
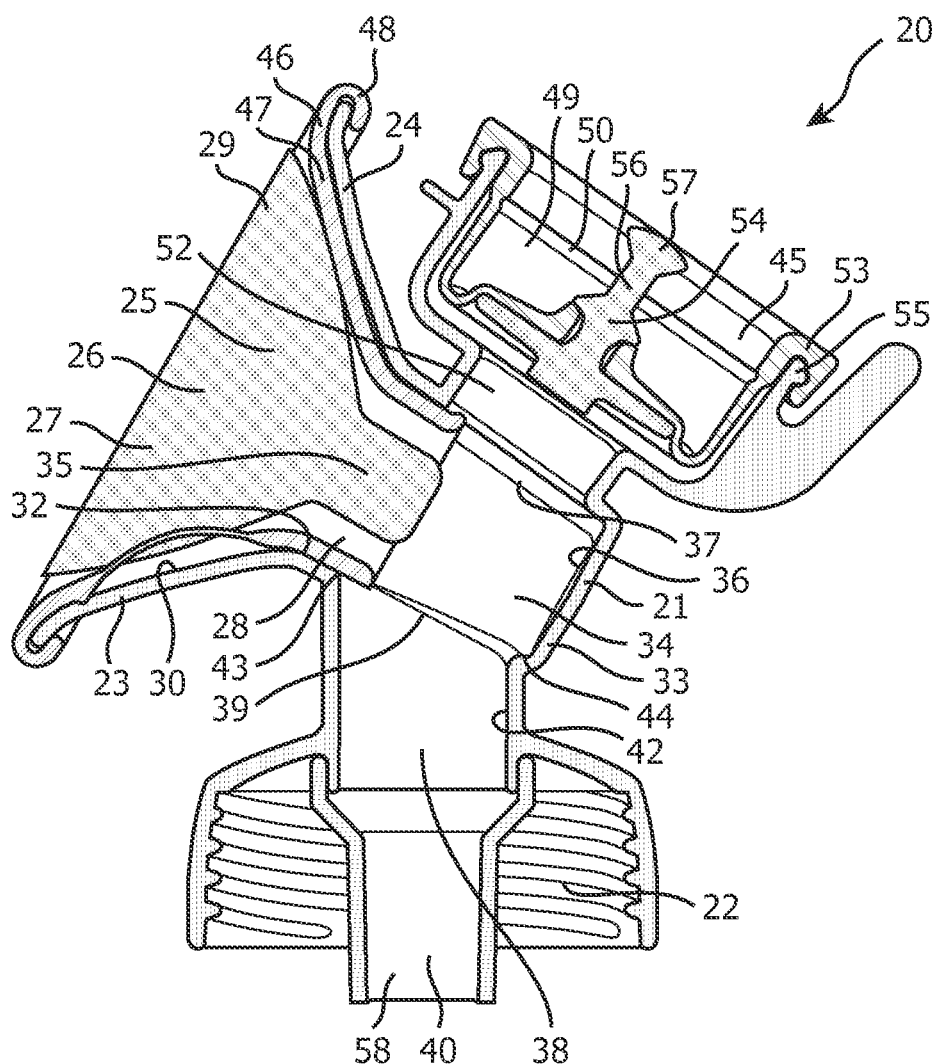
FIG. 3 shows a cross-sectional side view of a breast pump.

Referring now to FIG. 3, a breast pump unit 20 is shown. The breast pump comprises a main body 21 and a milk-receiving vessel (not shown). The milk receiving vessel, which may take the form of a feeding bottle for an infant or baby, is attached to the main body by a screw fitting 22, although it will be understood that alternative releasable attachment means may be used, such as clips (not shown).

A breast receiving funnel 23 extends from the main body 21 of the breast pump 20. The funnel 23 comprises an outer shell 24 and has a hollow breast receiving space 25 for receiving the breast of a user 26. The outer shell 24 extends from the main body 21 and is integrally formed therewith.

The breast receiving funnel 23 comprises a mouth section 27 and a neck section 28. The mouth 27 is conical and has an outer end 29 through which a user inserts a breast. An inner surface 30 of the mouth 27 converges from the outer end 29 towards the neck 28. The neck 28 is tubular with a circumferentially extending inner surface 32, and extends between the mouth 27 and the main body 21.

The mouth 27 and neck 28 are formed by the outer shell 24 and are integrally formed with each other and main body 21. The outer shell 24 of the funnel 23 and the main body 2 are formed from a rigid, non-deformable material, such as a rigid plastic, for ease of manufacture and to allow sterilization, although alternative suitable materials may be used.

Although in the present embodiment the funnel 23 is integrally formed with the main body 21 of the breast pump, it will be understood that in an alternative embodiment the funnel 23, or the mouth 27 of the funnel 23, is removably mounted thereto. Such a funnel 23 is removably mounted to the main body 21 of the breast pump to aid cleaning or sterilization of the funnel 23 and main body 21.

The main body 21 comprises an outer shell 33 and has a main chamber formed therein which acts as a nipple receiving chamber 34, as will become apparent hereinafter. The nipple receiving chamber 34 is cylindrical with an opening 35 to the funnel 23 formed at one end and an end wall 36 at an opposing end. A side wall 37 extends between the opening 35 and the end wall 36, and extends circumferentially to define the chamber 34.

The neck 28 of the funnel 23 communicates with the nipple receiving chamber 34 through the opening 35. A fluid passageway 38 extends from a lower side of the side wall 37 of the nipple receiving chamber 34. The nipple receiving chamber 34 and fluid passageway 38 are disposed above the milk receiving vessel so that milk flows directly to the milk receiving vessel. The fluid passageway 38 is tubular with a side wall 42, an aperture 39 at a first end of the fluid passageway 38 communicating with the nipple receiving chamber 34 and a second end 40 extending to the milk receiving vessel. A front edge portion 43 of the fluid passageway 38 extends to a front end of the nipple receiving chamber 34, such that the fluid passageway 38 extends adjacent to the opening to the funnel neck 28.

A rear edge portion 44 of the fluid passageway 38 extends to a rear end of the nipple receiving chamber 34, such that the fluid passageway 38 extends to proximate the end wall 36. Therefore, it will be appreciated that the aperture 39 to the fluid passageway 38 extends substantially across the lower side of the side wall 37.

The mouth and neck 27,28 together define the breast receiving space 25, and a fluid path is provided between the breast receiving space 25 defined by the funnel, the nipple receiving chamber 34 in the main body 21 and the milk receiving vessel (not shown), through the fluid passageway 38. The fluid path also enables a vacuum pump unit 45 extending from the main body 21 to create a negative pressure in the nipple receiving chamber 34 when a user's breast is disposed in the breast receiving space 25, as will be explained below.

An insert 46 is disposed in the mouth 27 of the funnel 23. The insert 46 has a circle symmetric flexible, deformable wall 47 extending around an inner portion of the mouth 27 of the funnel 23 from an outer end 48 into the neck 28 of the funnel 23, wherein it extends to the opening 35 between the neck 28 and the nipple receiving chamber 34. An inner face of the flexible, deformable wall 47 forms the inner surface of the funnel 23 against which a user's breast locates when the insert is disposed therein. An advantage of the insert 46 is that it acts as a cushion to comfort a user's breast when it is disposed therein, and may be deformable into the breast receiving recess 25 during use to apply a compressive force to the breast to aid the expression of milk from the breast.

The vacuum pump unit 45 extends from the main body 21, and is used to cyclically create a vacuum in the nipple receiving chamber 34 when operated. The vacuum pump unit 45 comprises a resilient, deformable diaphragm 49 disposed in a diaphragm chamber 50.

The diaphragm chamber 50 is spaced from the nipple receiving chamber 34 by a vacuum pathway 52. This ensures that components of the vacuum pump unit 45, including the diaphragm 49, do not rub against the user's nipple when it is disposed in the nipple receiving chamber 34 formed in the main body 21, and so does reduces a user's discomfort. In conventional breast pumps, the vacuum pump unit is generally formed in the main body of the breast pump and so a nipple extending into the main body would come into contact with the vacuum pump unit.

The vacuum pathway 52 is tubular and extends between the side wall 37 of the nipple receiving chamber 34 and a base wall 53 of the diaphragm chamber 50. The vacuum pathway 52 opens on an upper side of the side wall 37 of the nipple receiving chamber 34, diametrically opposite the fluid passageway 38. The vacuum pump unit 45 is arranged so that the diaphragm 49 does not extend into the vacuum pathway 52. Therefore, the nipple receiving chamber 34 is disposed between the vacuum pump unit and the collection vessel. Although the vacuum pathway 52 opens on an opposing side of the nipple receiving chamber 34 to the fluid passageway 38, it will be appreciated that the vacuum pathway 52 may open to the nipple receiving chamber 34 adjacent to the fluid passageway 38.

Figure 5:
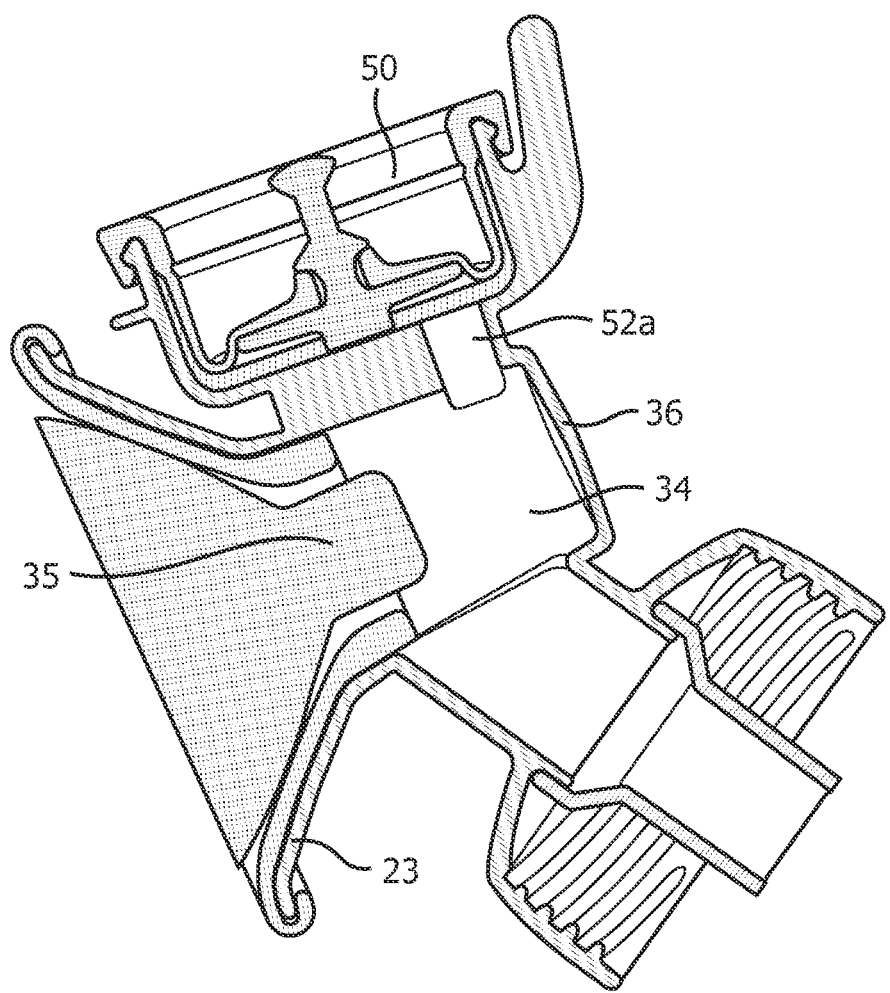
FIG. 5 is a cross-sectional side view of a breast pump according to another embodiment.
Figure 6:
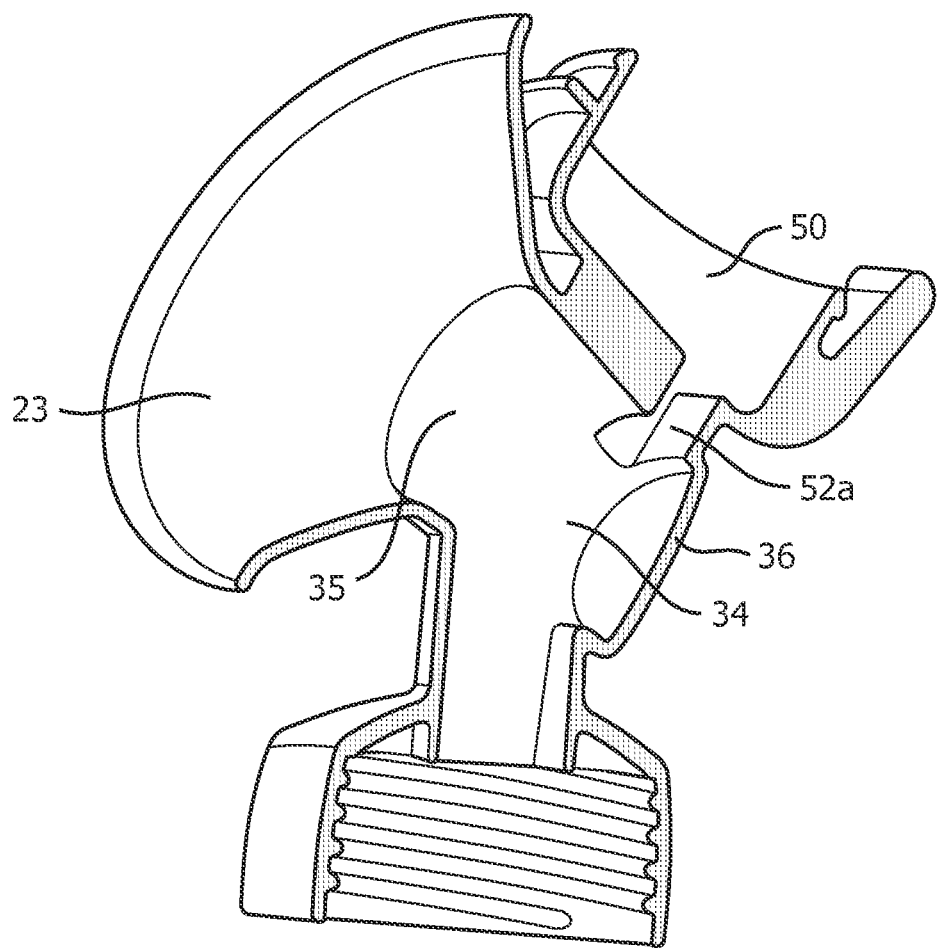
FIG. 6 is a perspective cross-sectional view of the breast pump shown in FIG. 5.

An alternative embodiment is shown in FIGS. 5 and 6. In this embodiment a vacuum pathway 52a is formed as an elongate slot extending between the side wall 37 of the nipple receiving chamber 34 and the base wall 53a of the diaphragm chamber 50. The elongate slot is disposed proximate to the end wall 36 and extends substantially parallel thereto so that the slot opens to the nipple receiving chamber 34 at the rear of the chamber, spaced from the opening 35 with the funnel 23. An advantage of this embodiment is that it further prevents discomfort on a user's nipple due to the diaphragm 49.

The diaphragm chamber 50 is cup shaped and the diaphragm is deformable in the diaphragm chamber 50 to act as a piston means. The diaphragm 49 is formed from an elastomeric material. A rim 53 of the diaphragm 49 is turned back on itself to receive an upper end 55 of the diaphragm chamber 50 to secure the diaphragm 49 in the diaphragm chamber 50. An actuating element 54 extends from the centre of the diaphragm 49. The actuating element 54 comprises a stem 56 and a bulbous end 57, distal to the diaphragm 49, which is attachable to a drive means (not shown), such as a handle (not shown) mounted to the breast pump 20, an external pump unit or a motor (not shown). The handle is manually operable to deform the diaphragm 49 and cyclically cause a vacuum in the diaphragm chamber 50, and therefore the nipple receiving chamber 34, as will be explained hereinafter. Alternatively, the motor is actuated to cyclically deform the diaphragm 34 and therefore create a vacuum. The motor is disposed in a motor unit (not shown) mounted to the vacuum pump unit 45. If an external pump unit (not shown) is employed, a tube communicates the electrically driven external pump unit with an upper side of the diaphragm chamber 50 and a cyclical vacuum is generated by the external pump unit to deform the diaphragm 49. Although it is envisaged that a diaphragm is used, in an alternative embodiment a vacuum may be formed in the nipple receiving chamber 34 without use of a diaphragm.

A valve 58 is disposed at an end of the fluid passageway 38, distal to the nipple receiving chamber 34. The valve 58 is a one way valve which seals the nipple receiving chamber 34 from the atmospheric pressure in the milk receiving vessel (not shown) when the vacuum pump unit 45 creates a vacuum in the nipple receiving chamber 34, but allows milk to flow to the milk receiving vessel.

Operation of the breast pump according to the above exemplary embodiment will now be described with reference to FIGS. 3 and 4.

To operate the breast pump 20, a user holds the breast pump 20 by the main body 21 and inserts a breast into the breast receiving space 25 formed by the funnel 23. The user's breast then extends into the funnel 23 and the inner surface of the mouth 27 of the funnel 23 locates against the user's breast 26 to form a seal.

As the user's breast is inserted into the funnel 23, the user's nipple is inserted into the neck 28 of the funnel 23, and extends through the neck 28, so that the user's nipple extends into the nipple receiving chamber 34 formed in the main body 21. It will be appreciated that the neck 28 has a small depth to allow the nipple to extend therethrough. Alternatively, the mouth of the funnel may open directly into the nipple receiving chamber 34 formed in the main body 21.

The end of the user's nipple is then disposed in the nipple receiving chamber 34. Therefore, the user's nipple is disposed over the aperture 44 to the fluid passageway 38. It will be appreciated that the front edge portion 43 of the fluid passageway aperture 39 extends to the front end of the nipple receiving chamber 34, adjacent to the opening to the neck of the funnel 23. Similarly, the rear edge portion 44 of the fluid passageway aperture 39 extends to the rear end of the nipple receiving chamber 34, such that the fluid passageway 38 extends to proximate the end wall 36. Therefore, it will be appreciated that the end of the user's nipple will be disposed over the aperture 39 to the fluid passageway 39, even if the length of the user's nipple varies.

The user then operates the breast pump 20. The user depresses and releases the handle (not shown) to cyclically actuate the vacuum pump unit 45 such that the actuating element 54 moves in a reciprocal manner the diaphragm, the diaphragm 49 repeatedly deforms to effect a cyclical vacuum in the diaphragm chamber 49. Alternatively, when the vacuum pump unit 45 is electrically driven, the user depresses a lever to activate the motor or external pump unit. The motor or external pump unit then drives the vacuum pump unit 45 in a reciprocal manner.

An advantage of the present arrangement is that the nipple receiving chamber is integrally formed in the main body of the breast pump, and so the main body itself is configured to prevent expressed milk from pooling against a user's breast, without any additional components. Therefore, further features of the breast pump may be positioned relative to the main body in an ergonomic manner to minimize physical effort and discomfort. For example, a handle extending from the main body is maintained in a desired operating position with respect to the user irrespective of the user's position.

As the vacuum pump unit 45 cyclically creates a vacuum in the diaphragm chamber 50, a reduced pressure is created in the nipple receiving chamber 34 due to the vacuum pathway 52 communicating the diaphragm chamber 50 with the nipple receiving chamber 34. Similarly, a reduced pressure is effected in the breast receiving space 25 defined by the funnel 23, which is sealed by a user's breast, and the fluid passageway 38, which is sealed by the valve 58 from the atmospheric pressure in the milk receiving vessel (not shown).

Milk is then expressed from the end of the user's nipple and flows into the nipple receiving chamber 34. As the end of the user's nipple is disposed over the fluid passageway 38, the expressed milk flows directly into the fluid passageway 38. Similarly, any milk which is ejected against the end wall 36 of the nipple receiving chamber 34 is urged to flow into the fluid passageway 38 due to the rear edge portion 44 of the fluid passageway aperture 39 extending to the rear end of the nipple receiving chamber 34, such that the fluid passageway 38 extends to proximate the end wall 36.

As the milk expressed from the user's nipple flows directly into the fluid passageway 38, the milk does not flow into the funnel 23 and so does not pool in the mouth 27 and neck 28 of the funnel.

In FIG. 3, the user's breast and the breast pump 20 are shown in use in a conventional position, in which the user leans forward to position their breast in the breast pump. In this position, milk expressed from the user's breast flows easily into the fluid passageway 38, without pooling anywhere else in the breast pump. However, with the above described arrangement, the user is able to orientate themselves in a number of positions.

Figure 4:
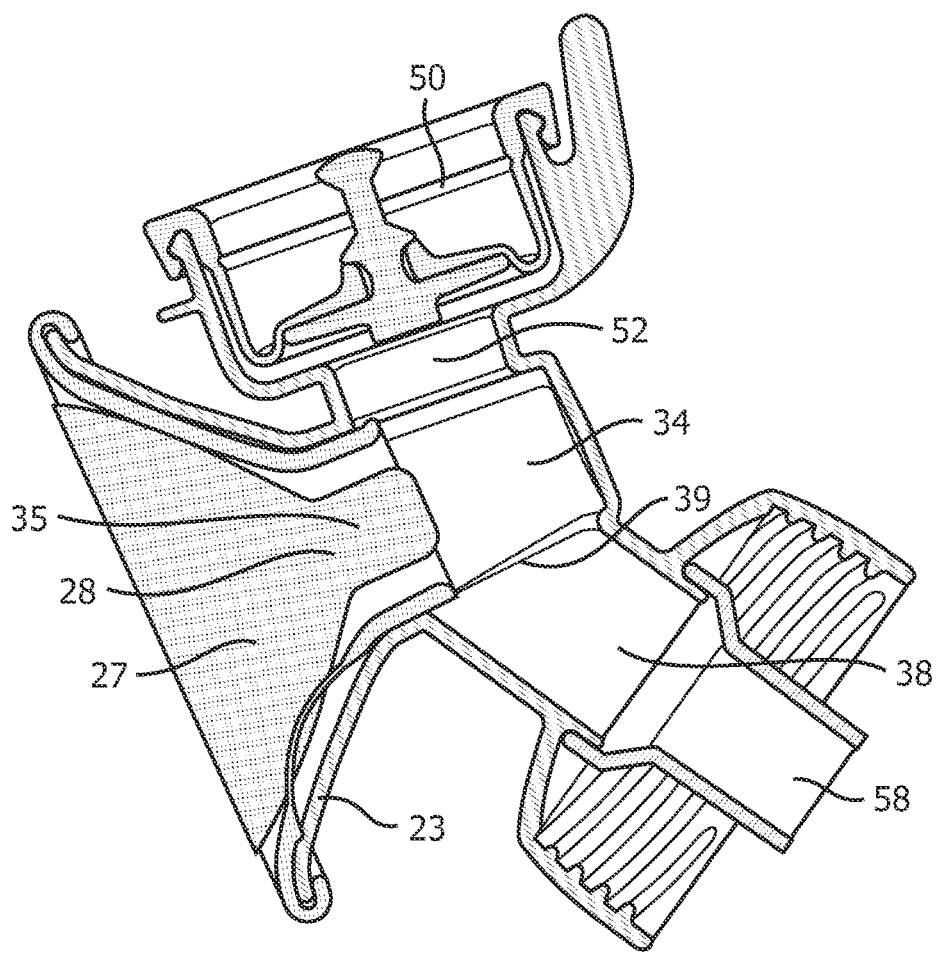
FIG. 4 shows a cross-sectional side view of the breast pump shown in FIG. 3 inclined at an angle.

In FIG. 4, the user's breast and breast pump are shown in use in a position in which the user leans backwards. In this position, the funnel 23 and main body 21 of the breast pump 20 are angled back towards the user. Expressed milk in a conventional breast pump used in this position would flow towards the user. However, with the present arrangement milk expressed from the user's breast flows into the fluid passageway 38 because the nipple is disposed over the aperture to the fluid passageway 38, and so milk cannot flow into the funnel 23 through the opening 35 thereto as all the milk expressed into the nipple receiving chamber 34 flows downwardly into the fluid passageway 38.

An advantage of the user being able to lean back and still enable expressed milk to flow to the milk receiving vessel without pooling elsewhere in the breast pump, is that it enables the user to maintain a more relaxed and comfortable expression position, which improves the user's 'let down' reflex, and reduces the user's time to milk ejection reflex. Furthermore, the user is able to use the breast pump for a longer duration as they are in a relaxed and comfortable expression position.

Furthermore, when a user removes the breast pump from their breast, there is little or no milk present in the funnel. Therefore, there is no milk loss as all the milk has flowed to the milk collecting vessel, and milk does not cause discomfort from wetting the user's skin and clothing.

The vacuum pathway 52 is disposed at an upper side of the nipple receiving chamber side wall 37, on an opposing side of the nipple receiving chamber to the fluid passageway 34. This ensures that during use milk expressed from a user's breast does not flow along the vacuum pathway 52 into the diaphragm chamber 50. Therefore, this helps prevent an unhygienic situation due to milk residue in the vacuum pump unit, and makes the breast pump easier to clean.

Milk flows into the fluid passageway 34 and collects therein without pooling in the funnel 23 and at the user's breast. Even when the one way valve 58 is closed milk expressed from the user's nipple is able to collect in the nipple receiving chamber 34 because the valve 58 is disposed at an end of the fluid passageway 38, distal to the nipple receiving chamber 34.

Furthermore, as the milk flows directly into the fluid passageway 38, it does not adhere to the inner surface of the funnel, and so less milk is wasted that does not flow to the milk collection vessel. Therefore, loss of milk expressed from a user's breast will be minimized.

Although in the above embodiments one fluid passageway extends from the nipple receiving chamber 34, it will be appreciated that in an alternative embodiment two or more fluid passageway sections (not shown) may extend from the nipple receiving chamber 34.

In the present embodiment, the main body 2 is formed from a transparent plastic. Therefore, it is possible for the user to view the nipple in the nipple receiving chamber during milk expression.

Additionally, the nipple receiving chamber 34 is disposed in the main body 21, and so the nipple is disposed in the main body 21 and not in the funnel 23 as in a conventional breast pump. Therefore, the volume of space in which the vacuum pump unit has to create a vacuum is reduced, which makes the vacuum pumping action more efficient and allows a lower pressure to be generated in the nipple receiving chamber 34.

Furthermore, when a user's nipple extends into the nipple receiving chamber 34, the nipple does not abut against or contact an inner surface of the main body or funnel, which restricts abrasion or rubbing of the user's nipple and therefore discomfort and/or soreness.

In addition, as the user leans back, the breast pump and milk receiving vessel attached thereto recline with the user. Therefore, the milk receiving vessel does not abut against the user's midriff and so does not limit the user's reclining position.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claims in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A breast pump comprising a main body, a breast receiving funnel extending from the main body, a nipple receiving chamber formed in the main body to receive a user's nipple, the nipple receiving chamber having an opening to the funnel through which a user's nipple is receivable, an end wall and an encapsulating side wall extending from the opening to the end wall, and a fluid passageway extending from the nipple receiving chamber for receiving milk expressed from a user's nipple characterized in that the fluid passageway connects to a portion of the side wall of the nipple receiving chamber between the opening and the end wall and in that a front edge portion of the fluid passageway extends to a front end of the nipple receiving chamber, wherein said portion of the side wall of the nipple receiving chamber connected to the fluid passageway comprises an aperture that extends substantially the entire length of the side wall.

2. A breast pump according to claim 1, wherein the mouth of the breast receiving funnel opens into the nipple receiving chamber.

3. A breast pump according to claim 1, wherein the mouth of the breast receiving funnel connects to the openings of the nipple receiving chamber adjacent to the fluid passageway.

4. A breast pump according to claim 1, wherein the funnel neck of the breast receiving funnel connects to the nipple receiving chamber adjacent to the fluid passageway.

5. A breast pump according to claim 1 wherein the main body further comprises a connection means for connecting a milk collection vessel, the fluid passageway communicating between the nipple receiving chamber and a milk collection vessel when a milk connection vessel is attached to the main body.

6. A breast pump according to claim 5, further comprising a one-way valve disposed in the fluid passageway.

7. A breast pump according to claim 1 further comprising a vacuum pump unit to generate a vacuum in the nipple receiving chamber.

8. A breast pump according to claim 7, wherein the vacuum pump unit comprises a deformable diaphragm, the deformable diaphragm being disposed in a diaphragm chamber spaced from the nipple receiving chamber.

9. A breast pump according to claim 7, wherein a vacuum pathway communicates the vacuum pump unit with the nipple receiving chamber.

10. A breast pump according to claim 9, wherein the nipple receiving chamber is disposed between the fluid passageway and the vacuum pathway.

11. A breast pump according to claim 9, wherein the vacuum pathway extends from the side wall of the nipple receiving chamber.

12. A breast pump according to claim 1, wherein the vacuum pathway extends from an opposing side of the nipple receiving chamber to the fluid passageway.

* * * * *